United States Patent [19]

Strohmaier

[11] Patent Number: 4,514,169

[45] Date of Patent: Apr. 30, 1985

[54] DENTAL HANDPIECE

[75] Inventor: Ernst Strohmaier, Schussenried, Fed. Rep. of Germany

[73] Assignee: Kaltenbach & Voigt GmbH & Co., Riss, Fed. Rep. of Germany

[21] Appl. No.: 592,692

[22] Filed: Mar. 23, 1984

[30] Foreign Application Priority Data

Sep. 9, 1983 [DE] Fed. Rep. of Germany ....... 3332628

[51] Int. Cl.³ .............................................. A61C 3/00
[52] U.S. Cl. ..................................................... 433/29
[58] Field of Search ........................................ 433/29

[56] References Cited

U.S. PATENT DOCUMENTS 2,038,911 4/1936 Stutz et al. ........................... 433/29
4,403,957 9/1983 Mossle et al. ........................ 433/29

FOREIGN PATENT DOCUMENTS 1068425 11/1959 Fed. Rep. of Germany ........ 433/29
1161157 8/1958 France ............................... 433/29

Primary Examiner—John J. Wilson
Attorney, Agent, or Firm—Scully, Scott, Murphy & Presser

[57] ABSTRACT

A dental handpiece, consisting of a connector portion and an elongated, exchangeable gripping sleeve portion coupled to the connector portion, including a treating implement arranged on the gripping sleeve end distant from the connector portion, wherein the connector portion incorporates a lightbulb or incandescent lamp, and the gripping sleeve portion includes a light conductor having the end thereof distant from the connector portions, directed towards the area of the implement, and whose end which is distant from the implement is suppliable with light from the incandescent lamp. The incandescent lamp will only burn when needed, but not when a gripping sleeve component without a light conductor is coupled to the connector portion, or even no gripping sleeve portion at all is present.

31 Claims, 10 Drawing Figures dental handpiece

BACKGROUND OF THE INVENTION

1. Field of the Invention

The present invention relates to a dental handpiece, consisting of a connector portion and an elongated, exchangeable gripping sleeve portion coupled to the connector portion, including a treating implement arranged on the gripping sleeve end distant from the connector portion, wherein the connector portion incorporates a lightbulb or incandescent lamp, and the gripping sleeve portion includes a light conductor having the end thereof distant from the connector portion, directed towards the area of the implement, and whose end which is distant from the implement is suppliable with light from the incandescent lamp.

2. Discussion of the Prior Art

A handpiece of that type has become known, for example, from the disclosure in German Laid-open Patent Application No. 31 32 995. Thus, there consists the need for coupling to the connector portion of such a handpiece, a gripping sleeve portion without a light conductor instead of a gripping sleeve portion with a light conductor, which is possible without any difficulty inasmuch as the coupling elements for those types of different gripping sleeve components are identical so as to; in essence, facilitate that kind of coupling action. Herein, however, it is disadvantageous that the lightbulb or incandescent lamp will burn in every instance; in effect, when a gripping sleeve component with a light conductor is coupled thereto, as well as when a gripping sleeve component without a light conductor is coupled thereto and, finally, also even when no gripping sleeve component at all is coupled thereto. Produced thereby is an unnecessarily high power consumption and an unnecessarily high degree of heating of the incandescent lamp while, moreover, its life expectancy is unduly shortened.

SUMMARY OF THE INVENTION

Accordingly, it is an object of the present invention, as set forth in specific detail hereinbelow, to eliminate the disadvantages of the prior art structures through the provision of a handpiece of the above-mentioned type in which there is afforded that the incandescent lamp will only burn when a gripping sleeve portion incorporating a light conductor is coupled to the connector portion.

The advantages which are achieved by means of the present invention can be essentially ascertained in that the incandescent lamp will only burn when needed, but not when a gripping sleeve component without a light conductor is coupled to the connector portion, or even no gripping sleeve portion at all is present.

BRIEF DESCRIPTION OF THE DRAWINGS

Reference may now be had to the following detailed description of exemplary embodiments of the invention, taken in conjunction with the accompanying drawings; in which.

DETAILED DESCRIPTION

Figure 1:
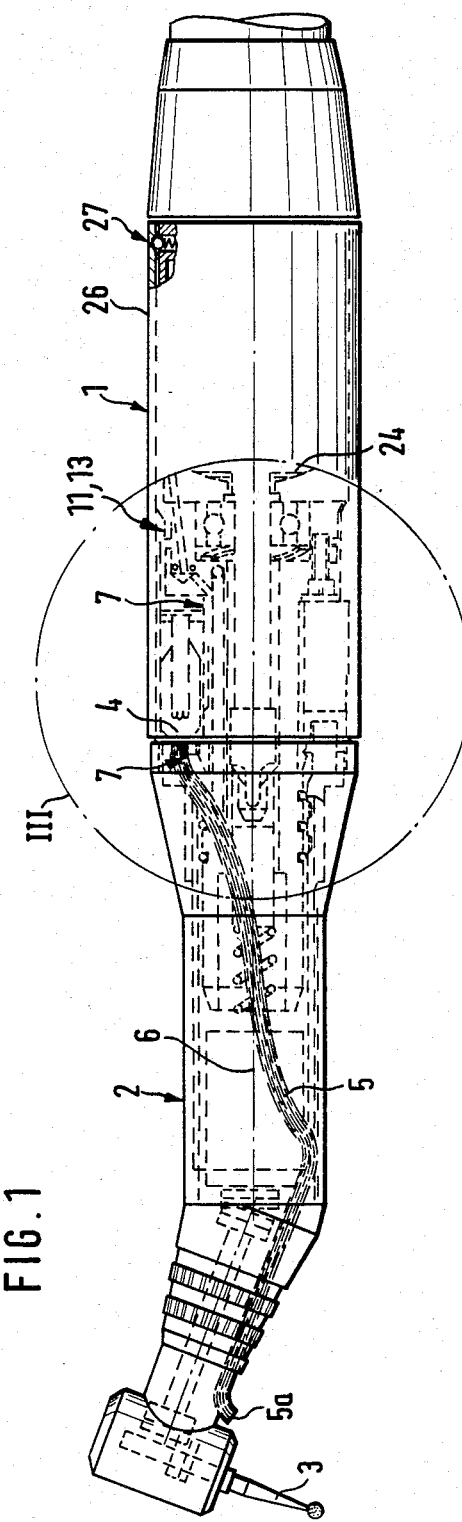
FIG. 1 illustrates a side view of a dental handpiece pursuant to the invention.

The dental handpiece pursuant to the invention consists of a connector portion 1 and an elongated, exchangeable gripping sleeve portion 2 which can be coupled to the connector portion, and which includes a treating implement 3 at the gripping sleeve end which is distant from the connector portion. The connector portion 1 incorporates an incandescent lamp or lightbulb 4 which, in the illustrated case, is arranged eccentrically interiorly of the connector portion in proximity to the outer wall structure thereof. The gripping sleeve portion 2, in the illustrated case, possesses a light conductor 5 in its interior, which at its end 5a distant from the connector portion is directed towards the area of the treating implement 3, and end of which distant from the implement is suppliable with light from the incandescent lamp 4.

The incandescent lamp 4 has switch contacts 11, 13 associated therewith, which are so movably arranged relative to each other whereby, at a coupled-on gripping sleeve portion 2, they are in a contact position affording power supply to the incandescent lamp 4; whereas at an uncoupled gripping sleeve portion 2, they are in a contact-breaking position interrupting the power supply, wherein at least the gripping sleeve portion 2 is provided with adjusting elements 4 which will effectuate movement of the contacts 11, 13 into the contact position, and upon uncoupling the return movement of the contacts into the contact-breaking position.

The contacts 11, 13 can be, basically, components of a suitable switch arrangement. Thus, for example, there can be provided a breaker switch on the connector portion 1. For this purpose, in the drawing there is illustrated a construction in which the contacts 11, 13 are arranged, on the one hand, on the connector portion 1 and, on the other hand, on the incandescent lamp 4, which is supported within the connector portion 1 for reciprocating movement in the direction of the longitudinal axis 6 of the handpiece, whereby the adjusting elements 7 are provided to implement the reciprocating movements of the incandescent lamp 4. Hereby, the adjusting elements 7 are formed by means of a pressure member 8 which is arranged on the gripping sleeve portion 2 and which effects the movement of the incandescent lamp 4 into the contacting position; and a resetting element 9 arranged on the connector portion 1 which effects the return movement of the incandescent lamp 4 into the contact-breaking position. In detail, the pressure member 8 is formed by an annular band or ring arranged at the end of the gripping sleeve portion 2 proximate the connector portion, and which extends axially away from the gripping sleeve portion and comes into contact with the incandescent lamp 4; whereas the resetting element 9 is formed by a pressure-spring acting on the incandescent lamp 4, and which, for example, is formed of a flat coil spring.

From the drawing there can be ascertained, that the incandescent lamp 4 is arranged in a housing 10 which is supported so as to be reciprocable within the connector portion 1 in the direction of the longitudinal axis 6 of the gripping sleeve portion, and on which there is actuated the pressure member 8 or the resetting element 9. Hereby, as shown in the drawing, the pressure element 8 comes into contact with the left-hand end surface of the housing 10 and the resetting element 9 with the right-hand end surface, as shown in the drawing.

The contacts 13 which are arranged on the connector portion 1 are interconnected with power supply lines 12. The contacts 11 which are associated with the incandescent lamp 4 are arranged on a projection 10b of the reciprocable housing 10, and which extends in a direction away from the gripping sleeve portion.

Suitably, the gripping sleeve portion 2 is unrestrictedly rotatable about the axis 6 of the handpiece relative to the connector portion 1. Thereby, the construction is such that the incandescent lamp 4 is rotatable about the axis 6 of the gripping sleeve portion 2 in conjunction with the latter relative to the connector portion 1, whereby the to-and-fro moveable contacts 11 are formed as slide contacts, and the contacts 13 which are fastened to the connector portion are constructed as contact rings, so that the housing 10 is rotatable along an arcuate path about the axis 6 of the gripping sleeve portion 2.

Figure 3:
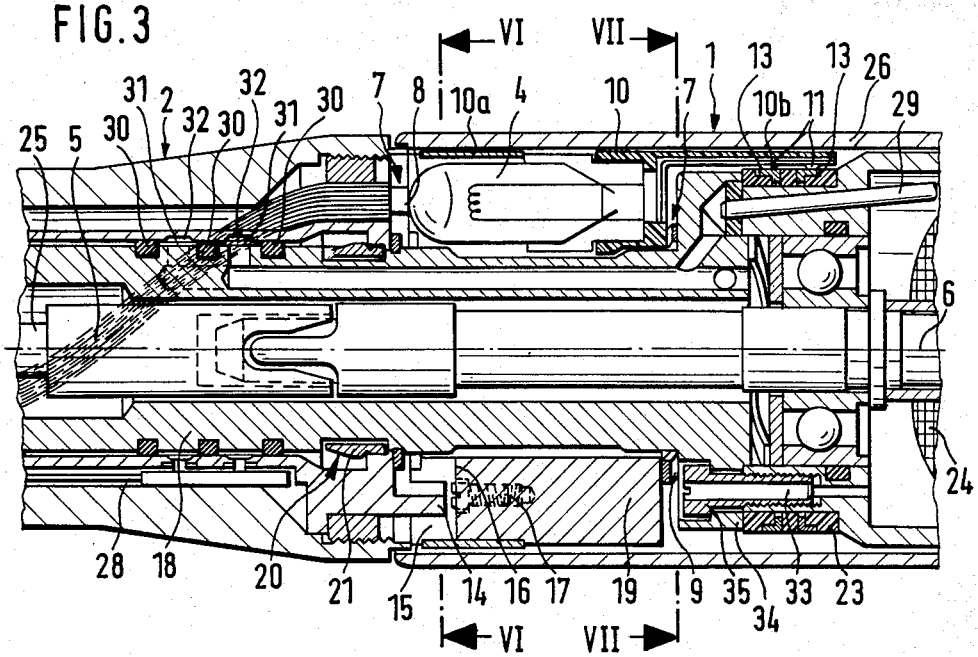
FIG. 3 is a sectional view, on an enlarged scale, view of the encircled portion III in FIG. 1.
Figure 4:
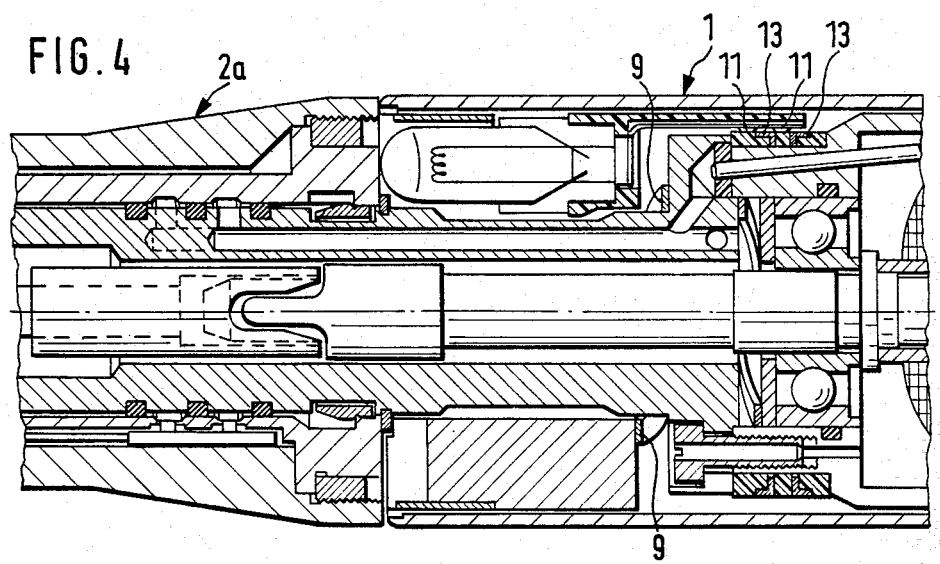
FIG. 4 illustrates a view similar to that of FIG. 3, with the difference that in lieu of the gripping sleeve portion with a light conductor, a usual gripping sleeve portion without a light conductor is coupled to the connector portion.
Figure 8:
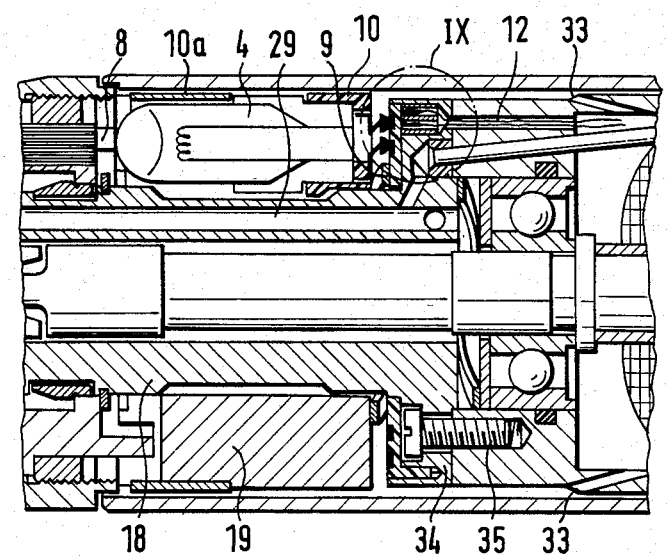
FIG. 8 illustrates a further embodiment modified relative to those illustrated in FIGS. 3 and 5.

As is illustrated in FIGS. 3, 4 and 8, the housing 10 is arranged at the end of the connector portion 1 towards the gripping sleeve portion and, for transmission of the rotational movement of the gripping sleeve portion 2, upon alignment of the incandescent lamp, through engaging means which engage through the end of the light conductor distant from the implement into complementary engaging means 14 on the gripping sleeve portion 2.

Figure 5:
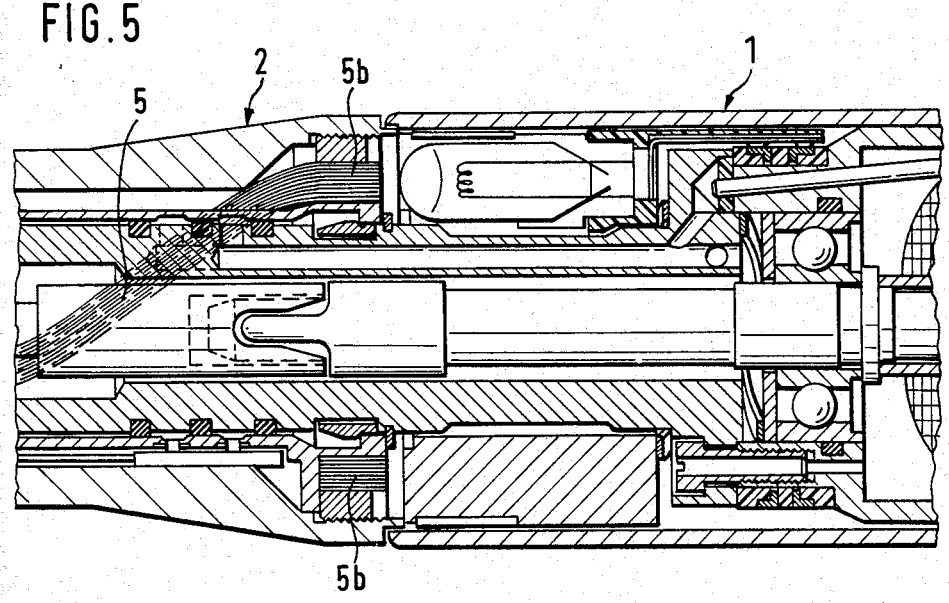
FIG. 5 is a view similar to that of FIG. 3 but showing a modified embodiment relative thereto.
Figure 6:
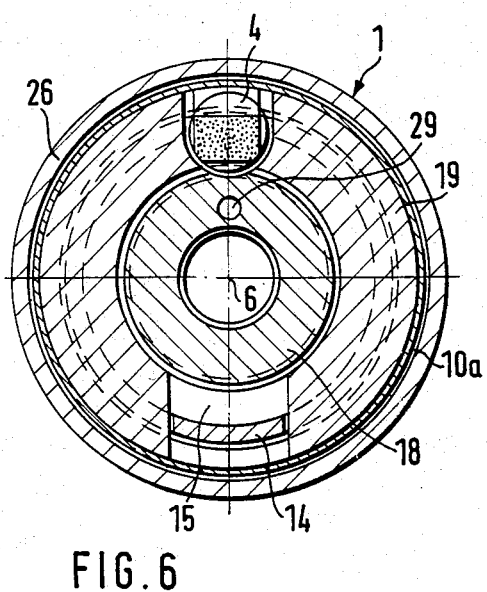
FIG. 6 is a sectional view taken along line VI—VI in FIG. 3.
Figure 7:
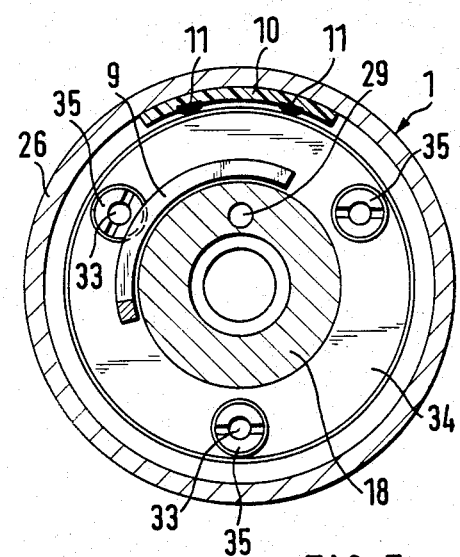
FIG. 7 is a sectional view taken along line VII—VII in FIG. 3.

In the embodiment shown in FIG. 5, there is not provided any such engaging means or complementary engaging means; for this purpose the end 5b of the light conductor 5 towards the connector portion is constructed as a lighting cable so that, in this manner, in each rotational position of the two handpiece portions 1, 2, there afforded the light transmission from the incandescent lamp 4 to the light conductor 5.

The incandescent lamp 4 is easily exchangeable; for example, at separated handpiece portions 1, 2, it can be pulled in the axial direction towards the left from the housing 10, and thereby withdrawn from the connector portion 1. There can also be provided a version of an exchangeable housing 10 for the lightbulb 4 or incandescent lamp as well as for the contacts 11 which are formed as slide contacts. In this instance, for the ready exchangeability of the housing 10, the latter has an easily removable, for example, snap ring-type securing element 10a associated therewith. Suitably, also the contacts 11 which are movable together with the incandescent lamp 4 and/or the contacts 13 which are fastened to the connector component are arranged so as to be exchangeable. For this purpose, for instance according to FIG. 9, the contacts 13 are connected by means of plug connectors 13a with the power supply lines 12 which are arranged in connector portion 1. The contacts 11 can be arranged in a similar manner.

The engaging means 15 of the housing 10 consists of a detent axially extending in its depth, and the complementary engaging means 14 on the gripping sleeve portion 2 of a similarly axially extending protuberance.

Suitably, pursuant to FIG. 3, the complementary engaging means 14 on the gripping sleeve portion 2 can concurrently form the pressure member 8 acting on the incandescent lamp 4 or on the housing 10, for which an adjusting element 17 is provided in the bottom 16 of the detent which can vary the height of the detent, such as, for example, a screw.

The housing 10 is arranged on a turning or swivel ring 19 which is rotatable about a stub shaft or trunnion-shaped extension 18 on the connector portion 1. The trunnion-shaped extension 18 can be inserted into the end of the gripping sleeve portion 2 which is distant from the implement, and as a result the gripping sleeve portion 2 is rotatable about the projection 18, which suitably possesses a circular cross-section.

In the embodiment pursuant to FIGS. 3 through 5, as a coupling element there is provided a locking arrangement 20 which maintains the extension 18 in its required inserted position, which consists of a radially resilient coupling ring 21, which is also freely rotatable and axially secured in the coupled condition and which encompasses the extension 18; which in the coupling condition representing the inserted position so load-transmissively and radially resiliently contacts the inner wall of the gripping sleeve portion 2, that the coupled portions 1, 2 are releasable from each through axial pulling apart upon overcoming the clamping force of the coupling ring 21. In the inserted position, the engaging means 15 are in engagement with the complementary engaging means 14, wherein the slide contacts 11 are in contact with the contact rings 13, so that the incandescent lamp 4 will burn and the end 5a of the light conductor 5 wich is distant from the connector portion will emit light.

The gripping sleeve portion 2 includes at least one medium supply conduit 28, for example, for a cooling medium, which is connectable through a connector conduit 29 of the connector portion 1 with a supply conduit (not shown) leading to a medium source (not shown) which is located externally of the handpiece. For this purpose, the gripping sleeve portion 2 and the connector portion 1 are provided with medium transfer means operative in every rotational position which, for example, pursuant to FIG. 3 is formed by a discharge opening 31 of the connector conduits 29 between two ring-shaped seal elements 30 encompassing the extension 18 and in contact with the inner wall of the gripping sleeve portion 2; and through an annular passageway 32 which is in communication with the medium supply conduit 28 in the region of the inner wall of the gripping sleeve portion 2. For example, pursuant to FIG. 3, the connector conduit 29 which conveys, for instance air, water or a spray consisting of an air-water mixture as a cooling medium, can be provided with a branch conduit 33 which leads to the incandescent lamp 4 for purposes of cooling thereof.

Figure 9:
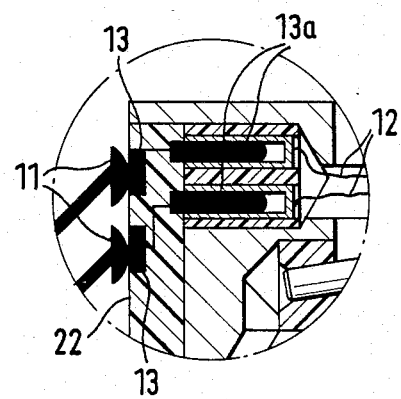
FIG. 9 is a sectional view, on an enlarged scale, of the encircled portion IX in FIG. 8.
Figure 10:
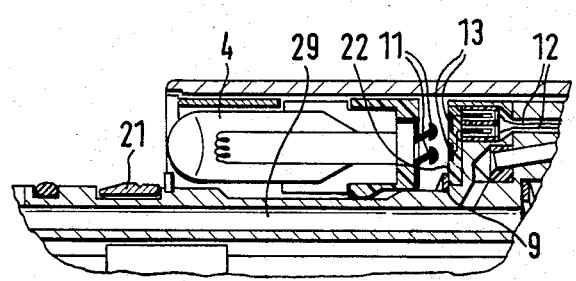
FIG. 10 is a fragmentary section of FIG. 8 with the incandescent lamp in a non-contacting position.

In the embodiment pursuant to FIGS. 9 and 10, the contacts 11, which are formed as slide contacts, are contacted by annular contact surfaces of the contacts 13 which are formed as contact rings, along a circumferential surface of the connector portion 1 located in a radial plane 22. In contrast therewith, in the embodiment pursuant to FIG. 3, the contacts 11 which are formed as slide contacts, are contacted by the annular contact surface of the contacts 13, which are constructed as contact rings, along a circumferential surface of the connector portion 1 which is located within a cylindrical sleeve ring 23.

FIGS. 3, 5, 8 and 9 illustrated the contact position effected by the pressure member 8, while FIGS. 4 and 10 show the contact-breaking position of the contacts 11, 13 effected by the resetting element 9 at an uncoupled gripping sleeve portion 2. Pursuant to FIG. 4, this contact-breaking position is also maintained when a usual gripping sleeve portion 2a, in effect, a gripping sleeve portion without a light conductor and without adjusting element (pressure member) is coupled to the connector portion.

Figure 2:
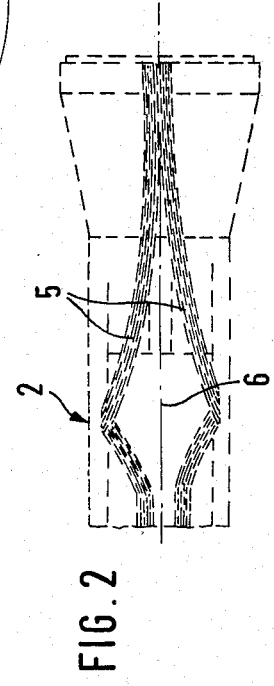
FIG. 2 illustrates a view, turned through an angle of 90°, of a segment of the gripping sleeve portion of the handpiece of FIG. 1.

As can be attained in particular from FIG. 1, arranged interiorly of the gripping sleeve portion within the interior of the connector portion 1, there can be coupled for example, drive means 24 formed by a drive motor, for example, transmission means 25 formed by a shaft for the drive of the respective rotatable treating implement 3, wherein the light conductor 5, which pursuant to FIG. 2 can also be formed of two wires, extends adjacent the drive transmission means 25.

The connector portion 1 possesses an outer sleeve 26 which radially covers the incandescent lamp 4 and, thereby, also the housing 10, and which has its end towards the gripping sleeve portion, in the coupled condition of the connector portion 1 and the gripping sleeve portion 2, contacting against the end of the gripping sleeve portion 2 remote from the implement; and in the uncoupled condition of the connector portion 1 and the gripping sleeve portion 2, can be withdrawn from the end of the connector portion 1, in a direction towards the gripping sleeve portion upon overcoming the clamping force of the locking device 27 which determines its inserted position. The trunnion-shaped extension 18 possesses, at the end thereof which is remote from the gripping sleeve portion, an annular flange 34 which contacts against the end wall of the connector portion towards the gripping sleeve portion, and by means of three screws 35 is fixedly interconnected with the above-mentioned end wall. Pursuant to FIGS. 3 and 4, the cooling medium branch conduit 33 leading to the incandescent lamp 4 is axially conducted through at least one of the screws 35.

What is claimed is:

1. In a dental handpiece, including a connector portion and an elongated, exchangeable gripping sleeve portion coupled to said connector portion, including a treating implement arranged on said gripping sleeve portion end distant from said connector portion, an incandescent lamp in said connector portion, and a light conductor in said gripping sleeve portion having the end of said light conductor distant from said connector portion directed towards the area of the implement, and the end of said light conductor distant from said implement being suppliable with light from said incandescent lamp; the improvement comprising in that switch contacts are operatively associated with said incandescent lamp, said switch contacts being movable relative to each other so as to be in a contact position facilitating power supply to said incandescent lamp, and wherein at least said gripping sleeve portion includes adjusting elements effectuating movement of said contacts into a contact position upon coupling of said gripping sleeve portion to said connector portion and effectuating the return movement of the contact into the contact-breaking position responsive to uncoupling of said connector and gripping sleeve portions, said contacts being arranged on respectively the connector portion and on said incandescent lamp, said contacts in said connector portion being supported therein for reciprocal motion in the direction of the longitudinal axis of said handpiece, and said adjusting elements effectuating the reciprocating motions of the incandescent lamp.

2. Handpiece as claimed in claim 1, wherein said adjusting elements include a pressure member on said gripping sleeve portion for effectuating the movement of said incandescent lamp to the contact position, and a resetting element on said connector portion for effectuating the return movement of the incandescent lamp into the contact-breaking position.

3. Handpiece as claimed in claim 2, wherein said pressure member comprises an annular plate arranged on the end of said gripping sleeve portion towards said connector portion, said annular plate extending axially from said gripping sleeve portion into contact against the incandescent lamp.

4. Handpiece as claimed in claim 3, comprising a housing reciprocably supported in said connector portion in the direction of the gripping sleeve portion axis, said incandescent lamp being arranged in said housing, and said pressure member and resetting element operatively acting on said housing.

5. Handpiece as claimed in claim 4, wherein said contacts reciprocable in conjunction with the incandescent lamp are arranged in said housing receiving said incandescent lamp.

6. Handpiece as claimed in claim 5, wherein said contacts which are movable in conjunction with incandescent lamp and the contacts which are fastened to said connector portion are exchangeable.

7. Handpiece as claimed in claim 6, wherein the contacts fastened to said connector portion are connected through plug connectors with power supply conduits arranged in said connector portion.

8. Handpiece as claimed in claim 2, wherein said resetting element comprises a pressure spring acting on said incandescent lamp.

9. Handpiece as claimed in claim 4, wherein said housing is arranged for rotation along an arcuate path about the longitudinal axis of said gripping sleeve portion.

10. Handpiece as claimed in claim 9, wherein said housing is arranged at the end of said connector portion towards said gripping sleeve portion, and includes engaging means for transmission of the rotational movement of the gripping sleeve portion in engagement with complementary engaging means on said gripping sleeve portion upon alignment of said incandescent lamp and the light conductor remote from said implement.

11. Handpiece as claimed in claim 10, wherein said engaging means on said housing comprise a dentent formed by an axially extending recess, and said complementary engaging means on said gripping sleeve portion comprise an axially extending protuberance.

12. Handpiece as claimed in claim 11, wherein said complementary engaging means on said gripping sleeve portion form said pressure member operatively acting on said incandescent lamp.

13. Handpiece as claimed in claim 11, comprising an adjustable adjusting element arranged in the bottom of said detent so as to change the depth thereof.

14. Handpiece as claimed in claim 13, wherein said adjusting element comprises a screw.

15. Handpiece as claimed in claim 4, wherein said housing is arranged on a swivel ring rotatably supported on a trunnion-shaped extension of said connector portion.

16. Handpiece as claimed in claim 15, wherein said extension is insertable into said gripping sleeve portion, and said gripping sleeve portion is rotatable about said extension.

17. Handpiece as claimed in claim 16, comprising a latching arrangement maintaining said extension in the inserted position in which said engaging means are in contact with the complementary engaging means, and said contacts on said incandescent lamp are in contact with the contacts of said connector portion.

18. Handpiece as claimed in claim 17, wherein said latching arrangement comprises a coupling ring encompassing said extension, and wherein said coupling ring in the coupled condition is freely rotatable and axially secured and resilient in the radial direction, and resiliently radially contacts in the coupled condition against the inner wall of the gripping sleeve portion in a force transmissive manner, wherein the coupled portions are releasable from each other through axial pulling apart upon overcoming the clamping force of the coupling ring.

19. Handpiece as claimed in claim 17, comprising an outer sleeve for the connector portion radially covering said incandescent lamp.

20. Handpiece as claimed in claim 19, wherein said outer sleeve has the end towards the gripping sleeve portion, in the coupled condition of the connector portion and the gripping sleeve portion, contacting against the end of the gripping sleeve portion remote from said implement.

21. Handpiece as claimed in claim 19, wherein the outer sleeve is withdrawable from the connector portion in the uncoupled condition of said connector portion and gripping sleeve portion.

22. Handpiece as claimed in claim 21, wherein said outer sleeve is withdrawable from said connector portion upon overcoming the clamping force of the latching arrangment determining its inserted position.

23. Handpiece as claimed in claim 21, wherein the outer sleeve is withdrawable from said connector portion in the direction towards the gripping sleeve portion.

24. Handpiece as claimed in claim 1, wherein said gripping sleeve portion is rotatable about its longitudinal axis relative to said connector portion.

25. Handpiece as claimed in claim 1, wherein said incandescent lamp is rotatable relative to said connector portion in conjunction with said gripping sleeve portion about the longitudinal axis of said gripping sleeve portion, and said reciprocable contacts being formed as slide contacts and the contacts fastened to said connector portion comprising contact rings.

26. Handpiece as claimed in claim 25, wherein said housing for said incandescent lamp and the contacts forming said slide contacts are arranged for interchangeability.

27. Handpiece as claimed in claim 26, wherein a readily releasable securing element is associated with said housing.

28. Handpiece as claimed in claim 25, wherein the contact rings include annular contacting surfaces which contact the slide contacts and are arranged on a circumferential surface of the connector portion in one radial plane.

29. Handpiece as claimed in claim 25, wherein the contact rings include annular contact surfaces which are in contact with the slide contacts and are arranged on a circumferential surface of the connector portion within a cylindrical sleeve ring.

30. Handpiece as claimed in claim 1, wherein the the gripping sleeve portion has drive transmission means arranged therein for the treating implement adapted to be coupled with drive means in the connector portion, wherein the light conductor extends adjacent the drive transmission means.

31. In a gripping sleeve component adapted to be exchangeably coupled to a drive component to form a dental handpiece, and which includes a treating implement, said drive component including an incandescent lamp and said gripping sleeve component including a light conductor having one end directed towards the treating implement, and wherein the end of said light conductor remote from said implement is suppliable with light from said incandescent lamp; the improvement comprising in that switch contacts are associated with said incandescent lamp, said switch contacts being displaceable relative to each other so as to be in a contact position providing a power supply to the incandescent lamp in the coupled position of said gripping sleeve component and being in a contact-breaking position to inhibit the power supply in the uncoupled position of said gripping sleeve component, a housing reciprocable in the direction of the axis of the gripping sleeve component, said incandescent lamp being arranged in said housing, a pressure member of said gripping sleeve component on said housing effectuating the movement of the incandescent lamp into the contact position, and a resetting element on said drive component for effectuating the return movement of the incandescent lamp into the contact as breaking position; the incandescent lamp is arranged at said housing for rotation along an arcuate path about the gripping sleeve component axis being rotatable relative to the drive component in conjunction with the gripping sleeve component about the gripping sleeve component axis, said reciprocable contacts being slide contacts and the contacts fastened to the drive component being contact rings, wherein the housing at the end of the drive component towards the gripping sleeve component is provided with engaging means complementary engaging means on said gripping sleeve component upon alignment of the incandescent lamp and the light conductor end distant from the implement, the housing and the gripping sleeve component being rotatable about an extension on said drive component insertable into the gripping sleeve component, and a latching means formed as a spring ring for maintaining the extension into the inserted axial position, wherein in the inserted position the engaging means are in engagement with the complementary engaging means, and the contacts of said incandescent lamp are in contact with the contacts of the drive component, wherein media transmission means are accessible in every rotational position through media conduits in the drive component and in the gripping sleeve component, and wherein drive means arranged in said drive component are coupled with drive transmission means for the implement arranged in said gripping sleeve component.

* * * * *